(12) United States Patent
Rahman et al.

(10) Patent No.: US 6,821,259 B2
(45) Date of Patent: Nov. 23, 2004

(54) ORTHOSIS DEVICE

(75) Inventors: Tariq Rahman, Wilmington, DE (US); Whitney Sample, Wilmington, DE (US)

(73) Assignee: The Nemours Foundation, Wilmington, DE (US)

( * ) Notice: Subject to any disclaimer, the term of this patent is extended or adjusted under 35 U.S.C. 154(b) by 497 days.

(21) Appl. No.: 10/024,133

(22) Filed: Dec. 21, 2001

(65) Prior Publication Data

US 2003/0023195 A1 Jan. 30, 2003

Related U.S. Application Data

(60) Provisional application No. 60/308,109, filed on Jul. 30, 2001.

(51) Int. Cl.[7] ................................................ A61H 1/00
(52) U.S. Cl. .............................. 601/24; 602/20; 601/33
(58) Field of Search .............................. 602/20, 19, 16, 602/6; 601/33, 24, 23, 26; 482/67, 100, 124, 131, 139

(56) References Cited

U.S. PATENT DOCUMENTS

| | | | | |
|---|---|---|---|---|
| 4,651,719 A | * | 3/1987 | Funk et al. | 601/33 |
| 4,975,016 A | * | 12/1990 | Pellenc et al. | 414/501 |
| 5,020,790 A | * | 6/1991 | Beard et al. | 482/4 |
| 5,417,643 A | * | 5/1995 | Taylor | 601/33 |
| 5,466,213 A | * | 11/1995 | Hogan et al. | 601/33 |
| 6,565,493 B1 | * | 5/2003 | Geh | 482/122 |

OTHER PUBLICATIONS

Transaction of the ASME, Journal of Mechanical Design, vol. 117, Dec. 1995, pp. 655–658, "A Simple Technique to Passively Gravity–Balance Articulated Mechanisms". Tariq Rahman et al.*
Journal of Rehabilitation Research and Development vol. 37 No. 6, Nov./Dec. 2000 pp. 675–680, "A body–powered functional upper limb orthosis" Tariq Rahman et al.
Transactions of the ASME, Journal of Mechanical Design, "A Simple Technique to Passively Gravity–Balance Articulated Mechanisms" Tariq Rahman et al, pp. 655–658, vol. 117, Dec. 1995.

* cited by examiner

Primary Examiner—Nicholas D. Lucchesi
Assistant Examiner—Huong Q. Pham
(74) Attorney, Agent, or Firm—McGuire Woods LLP

(57) ABSTRACT

An orthosis device generally includes two limb sections pivotably attached to each other in at least one degree of freedom and adapted for insertion of or attachment to adjacent portions of a limb of a user. Each limb section further includes a four-bar linkage and a spring member adapted to provide an equilibrium-inducing force corresponding to a combined weight of the limb section and the limb inserted therein or attached thereto. The equilibrium-inducing force allows every point in three-dimensional space to be a balanced position, such that a user with muscular abnormalities can move his or her limbs and hold them in place. A pivotable shoulder bracket for attaching the orthosis device to a wheelchair may also be provided. Furthermore, the orthosis device can be adapted to accommodate individuals of varying weight or with varying levels of disability by adjusting the spring member or providing powered actuators and force sensors.

20 Claims, 7 Drawing Sheets

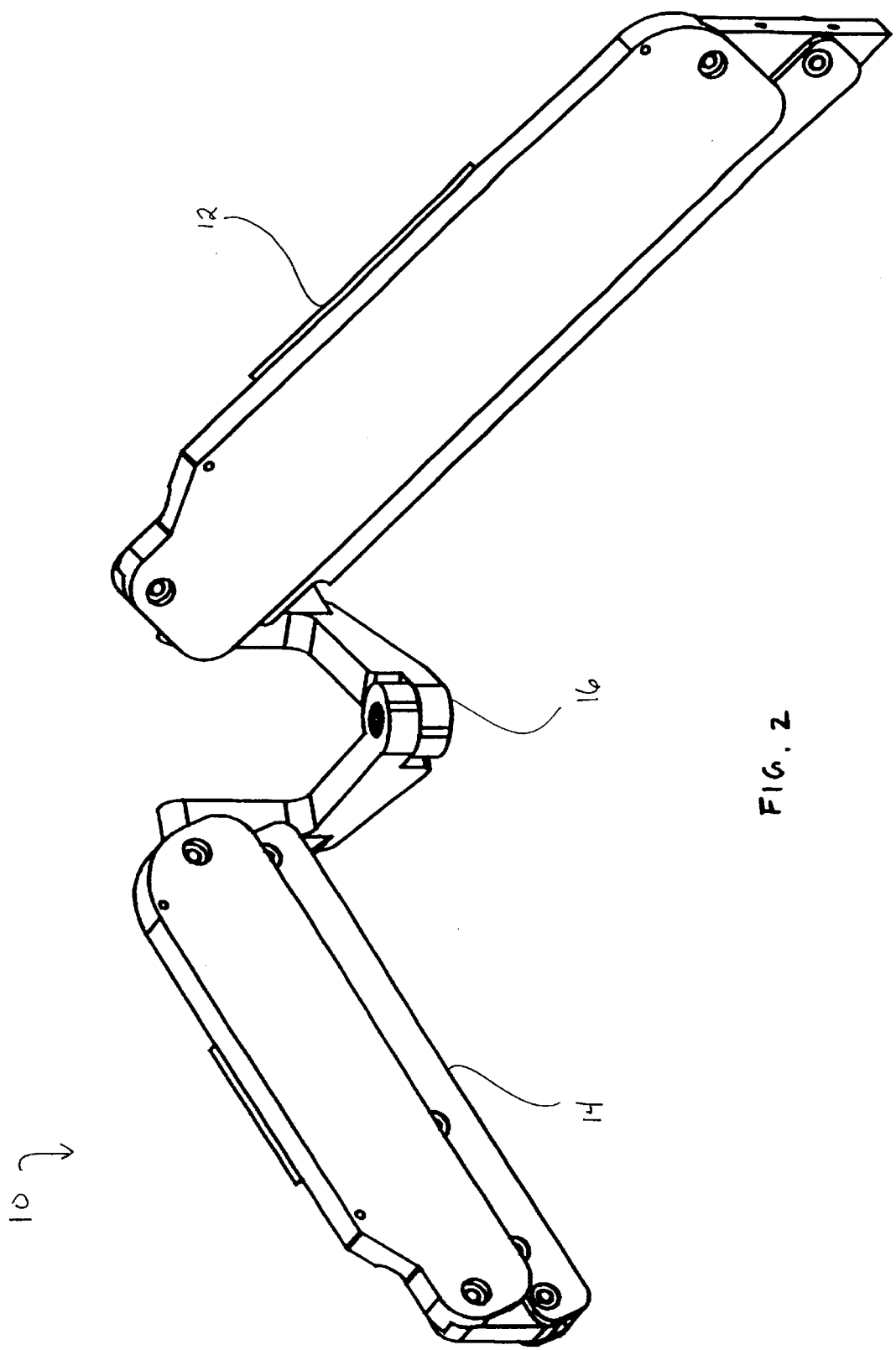

ORTHOSIS DEVICE

This application claims priority under 35 U.S.C. §§ 119(e) and 120 of U.S. Provisional Patent Application Ser. No. 60/308,109, filed Jul. 30, 2001, the content of which is hereby incorporated by reference.

BACKGROUND OF THE INVENTION

1. Field of the Invention

The present invention relates generally to assistive medical devices. More particularly, the present invention relates to a device for assisting and augmenting the movements of a person with neuromuscular abnormalities or weakness.

2. Background Description

Individuals with neuromuscular abnormalities, such as anterior horn cell disease or muscular disorders (e.g., Muscular Dystrophy), often lose the ability to place their limbs in space due to the weakening of their proximal muscles. Typically, the muscles of these individuals become so weak that they cannot support their arms against gravity, thereby making it difficult to perform routine tasks such as eating.

An orthosis is an exoskeletal device that is attached to flail or weakened limbs to augment strength deficiency. Articulated upper limb orthoses, ranging from the mobile arm support to electrically powered wrist-hand orthoses, have been investigated for a number of years.

Among the earliest and most accepted devices is the Balanced Forearm Orthosis ("BFO"), also called the mobile arm support. The BFO, a passive (e.g., body-powered) device was developed in 1965, and provides people with weak musculature the ability to move their arms in a horizontal plane. Two linkages having joints along the vertical axes accomplish this task. One end of the BFO is attached to a wheelchair, while the other end is connected to a trough into which a person places his or her forearm. The trough uses a fulcrum at mid-forearm that permits the hand to elevate if the shoulder is depressed. The BFO allows a person to move horizontally, for example, over a lap tray, and to use compensatory movements to attain limited movement in the vertical direction.

An enhanced version of the BFO allows vertical movement by providing a horizontal joint at the base. Attaching rubber bands to the joint compensates for the weight of the arm. Due to the inexact gravity compensation that results, this device is rarely prescribed. The majority of BFO users settle for planar movement and rely on compensatory body movements to achieve vertical motions.

Various forms of overhead slings that allow for movement in three dimensions have also been used to assist arms with proximal weakness. These devices, in addition to being aesthetically unappealing, are prone to oscillations when the arm is moved. One such overhead device is the Musgrave orthosis, which uses a weight at the back of a wheelchair to counterbalance the arm.

The first computerized orthosis was developed at the Case Institute of Technology in the early 1960s. The manipulator was configured as a floor mounted, four degree-of-freedom, externally powered exoskeleton. Control of this manipulator was achieved using a head-mounted light source to trigger light sensors in the environment.

Rancho Los Amigos Hospital continued the Case orthosis and developed a six degree-of-freedom, electrically driven "Golden Arm." The Rancho "Golden Arm" had a configuration similar to the Case arm, but was without computer control. It was significant, however, in that it was mounted on a wheelchair and was found to be useful by people who had disabilities with intact sensation resulting from polio or multiple sclerosis. The Rancho "Golden Arm" was controlled at the joint level by seven tongue-operated switches, which made operation very tedious. The "Golden Arm" was subsequently modified to add computer control and input from eye trackers.

In 1975, the Burke Rehabilitation Center modified the BFO by adding actuators. Direct current motors powered the Burke orthosis, with five degrees-of-freedom, including pronation/supination and elbow flexion/extension. However, control was maintained through use of a joystick, control pad, or various microswitch assemblies, making it a less-than-ideal interface.

Examples of other orthoses that have not gone beyond the prototype stage include the hybrid arm orthosis, which was externally powered and controlled by a combination of contralateral shoulder movement and air switches operated by the head, and the powered orthotic device for the enhancement of upper limb movement. This latter project was conducted at The Hugh Macmillan Rehabilitation Center and targeted people with amyotrophic lateral sclerosis. This mechanism allowed three degrees-of-freedom, used external power, and was controlled by signals from the eyebrows.

While the existing orthosis devices have advanced the state of the knowledge in design of orthoses that interact with humans with disabilities, the technology has yet to make a significant impact on the lives of people with disabilities. This is in large part due to the complex control requirements of the devices and the prohibitive cost of powered devices.

SUMMARY OF THE INVENTION

It is an object of the present invention to provide an orthosis device with a natural human-machine interface.

Another object of the present invention is to provide a fully functional yet cost-efficient orthosis device.

Yet another object of the present invention is to provide a gravity-balanced sense of "floatation" that will allow a person with neuromuscular weakness to move his or her limbs with minimal effort.

Still another object of the present invention is to provide an orthosis device adaptable to a range of user weights and disabilities.

The present invention is an orthosis device for providing a gravity-balanced equilibrium for a limb of a user. The orthosis device generally includes two limb sections that are pivotably connected in at least one, and preferably two, degrees of freedom. Each of the two limb sections comprises a four-bar linkage and a spring member adapted to provide an equilibrium-inducing force corresponding to a combined weight of the limb section and the user's limb attached thereto. The equilibrium-inducing force allows every position in three-dimensional space to be a balanced position, such that minimal effort is required to move the limb or hold it in place.

Two mounting mechanisms attached to each limb section are used to attach the spring member. At least one of the mounting mechanisms may be adjustable to pre-stress the spring member, allowing a single embodiment of the orthosis device to be used for individuals of a range of weights. Furthermore, individuals with varying degrees of muscular degeneration can be accommodated by including force sensors and power actuators.

The orthosis device, in embodiments, includes a shoulder bracket for mounting the orthosis device on a wheelchair. The shoulder bracket includes several pivotably connected links, which adds additional degrees of freedom to the orthosis device. Thus, the orthosis device according to the present invention allows for anatomical movement in essentially four degrees of freedom: two at the elbow and two at the shoulder.

BRIEF DESCRIPTION OF THE DRAWINGS

FIG. 1b is a diagram of the geometry of the structure shown in FIG. 1a;

FIG. 2 is perspective view of the orthosis device with limb section covers;

DETAILED DESCRIPTION OF THE PREFERRED EMBODIMENT OF THE INVENTION

Figure 1A:
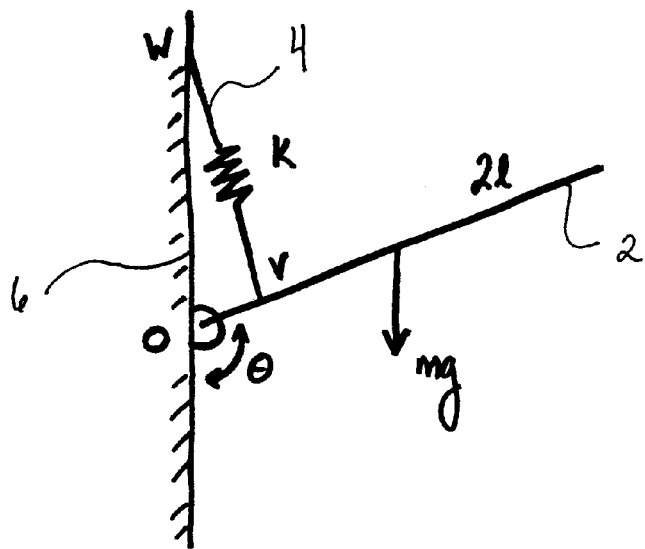
FIG. 1a is a schematic diagram illustrating the gravity-balancing principle utilized by the present invention.
Figure 1B:
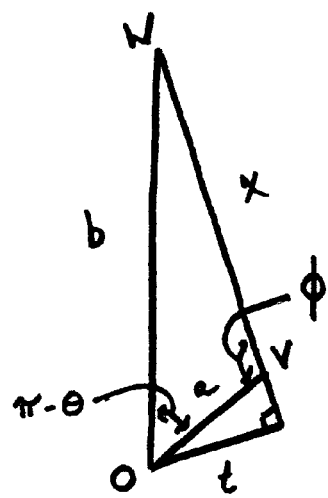

Referring now to the Figures and more particularly to FIGS. 1a and 1b, there is shown a schematic diagram illustrating the gravity-balancing principle utilized by the present invention. FIG. 1a illustrates a rigid link 2 pinned at axis "O" and held by a linear spring 4 at position "V," which is attached to a vertical wall 6 at position "W." Link 2 has a length 2l and mass m, while spring 4 has a spring constant k. For the system to be in equilibrium, $M_O$, the moment about "O," must be 0. From FIG. 1b, it can be seen that $$M_O = mgl \sin \theta - k(x-x_0)t = 0.$$

For $\theta \neq 0$, this reduces to $$Mgl = \frac{k}{x}(x - x_0)ab.$$

If $x_0=0$, the equation further reduces to $$k = mgl/ab. \quad (1)$$

Equation (1) shows that the stiffness k becomes a constant independent of the angle $\theta$ of link 2. This is achievable only if the unstretched length $x_0$ of spring 4 is chosen to be 0. This condition may be physically realized if spring 4 is placed outside the line V-W. Therefore, by choosing a spring 4 of stiffness k according to Equation (1), and placing spring 4 outside of the line V-W connecting link 2 and wall 6, link 2 can be perfectly balanced for all angles $\theta$ from 0° to 180°.

Though FIGS. 1a and 1b illustrate gravity-balancing of a single link only, one skilled in the art will understand how to extend the one-link solution above to arrive at the generalized solution $$k_t = (g/a_t b_t)\left(m_t l_t + \sum_{s=t+1}^{n} 2m_s l_s\right) \quad (2)$$

for n links connected in series, where $1 \leq t \leq n$. One skilled in the art will also recognize that each link comprises a four-bar mechanism to ensure that vertical members exist at the end of each link.

Turning now to FIG. 2, there is shown an orthosis device 10 according to the present invention. Orthosis device 10 generally includes a first limb section 12 and a second limb section 14 adapted to fit adjacent portions of a limb of a user. For example, in a preferred embodiment of the invention herein described, first limb section 12 is adapted to fit a user's upper arm, while second limb section 14 is adapted to fit the user's forearm. However, first and second limb sections 12 and 14 may be adapted to fit other limbs (e.g., upper and lower legs) within the spirit of the invention. First and second limb sections 12 and 14 are pivotably connected in at least one degree of freedom, and are preferably pivotably connected in two degrees of freedom via elbow joint 16, which is generally aligned with the anatomical elbow. Elbow joint 16 can be any well known hinge mechanism, and provides orthosis device 10 with rotation about a vertical axis at a point generally corresponding to the anatomical elbow. Second limb section 14 is also fitted with a trough (not shown) that the user places his or her forearm into, though other methods of attaching orthosis device 10 to the user are contemplated (e.g., strapping it directly to the limb via a belt-buckle type arrangement).

Figure 3:
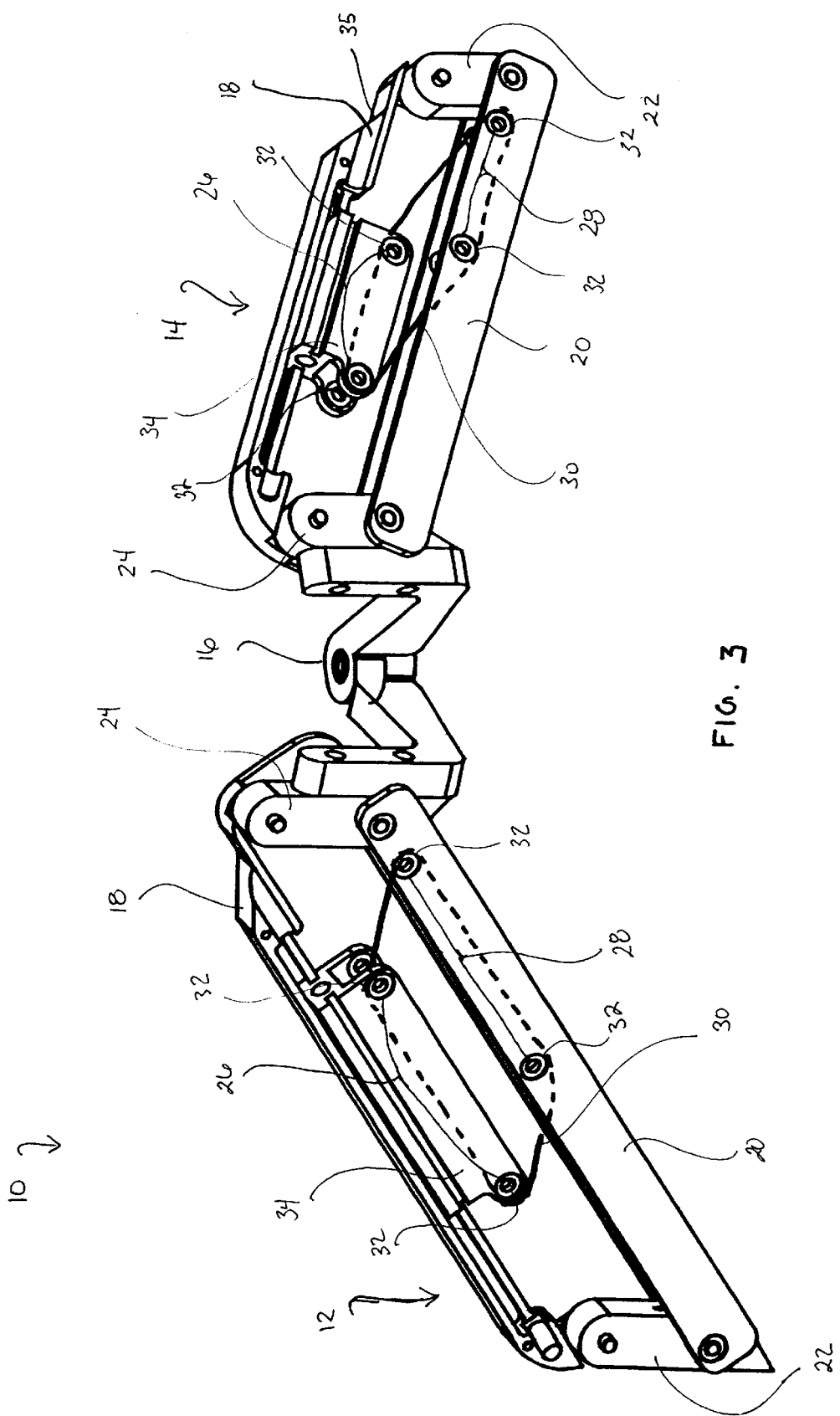
FIG. 3 is a perspective view of the orthosis device with the limb section covers removed.

FIG. 3 shows orthosis device 10 with covers removed in order to better illustrate the similar inner structures of first and second limb sections 12 and 14. Each section includes a first link 18, a second link 20, a third link 22, and a fourth link 24. First and second links 18 and 20 are substantially parallel to each other, as are third and fourth links 22 and 24. Third and fourth links 22 and 24 pivotably connect corresponding opposing ends of first and second links 18 and 20 by any well known hinge mechanism, thereby defining a four-bar linkage in each of first and second limb sections 12 and 14. One skilled in the art will be familiar with a four-bar linkage and the kinematics thereof.

First and second limb sections 12 and 14 further include a first mounting mechanism 26, a second mounting mechanism 28, and a spring member 30 having a spring constant k. First and second mounting mechanisms 26 and 28 are adapted for attachment of spring member 30 thereto, preferably via a pair of mounting posts 32 separated from each other by a distance determined based upon the spring stiffness k of spring member 30. Spring member 30 may be an elastic cord (e.g., a bungee cord) stretched between mounting posts 32 of the mounting mechanisms 26 and 28, or another type of spring (e.g., a coil spring). The elastic cord embodiment is preferred, however, because of the ability of an elastic cord to stretch over a post (e.g., mounting posts 32) and the superior elastic properties thereof (e.g., an elastic cord will stretch more than a coil spring with lower initial force requirements). Spring member 30 is selected to provide an equilibrium-inducing force corresponding to a combined weight of limb section 12 or 14 and the limb therein, as will be described below.

In one preferred embodiment of the invention, first and second mounting mechanisms 26 and 28 are mounted on first and second links 18 and 20, respectively, such that they are offset from each other along a length of the limb section 12 or 14. Additionally, the position of first mounting mechanism 26 is adjustable along the length of link 18. This is preferably accomplished by providing first mounting mechanism 26 on a carriage 34 attached to first link 18, the position of which is controlled via a lead screw 35 or other mechanism provided on first link 18. By adjusting the position of carriage 34 along link 18, spring member 30 can be pre-stressed by an amount corresponding to the weight of the limb of the user, thereby allowing a single orthosis device 10 to be used by users having a range of weights.

Figure 4:
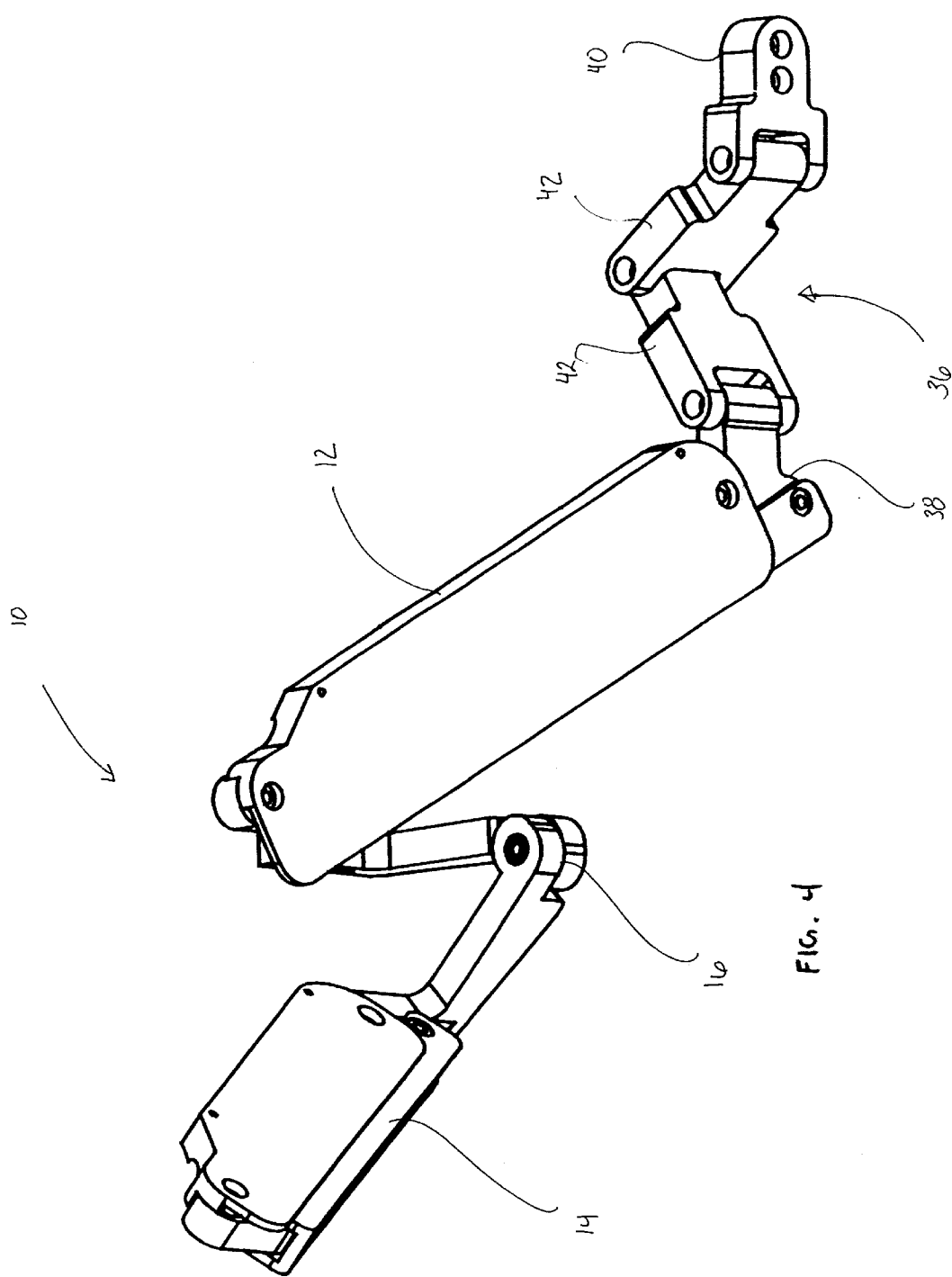
FIG. 4 is a perspective view of the orthosis device with shoulder bracket.
Figure 6:
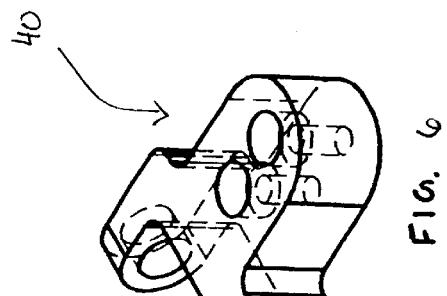
FIG. 6 is a perspective view of the free end link of the shoulder bracket.
Figure 7:
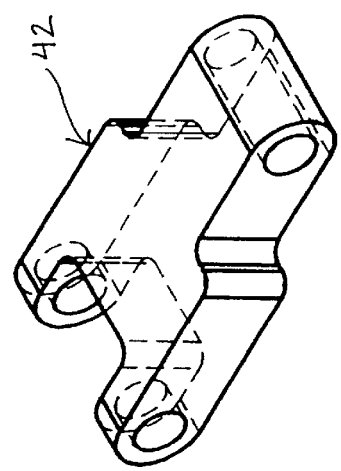
FIG. 7 is a perspective view of an interior shoulder bracket link.
Figure 5:
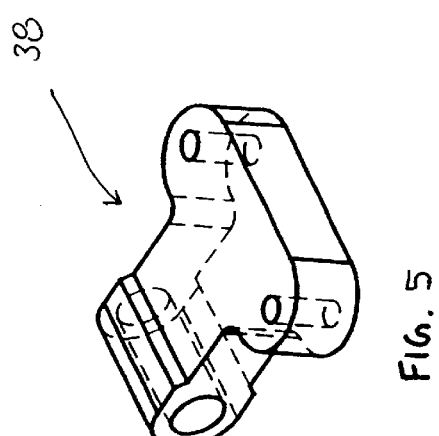
FIG. 5 is a perspective view of the attached end link of the shoulder bracket.

Orthosis device 10 also may include shoulder bracket 36, as shown in FIGS. 4–7. Shoulder bracket 36 attaches at an attached end link 38, shown in FIG. 5, to the proximal end of first limb section 12, and is adapted at a free end link 40, shown in FIG. 6, for attachment to a chair (e.g., a wheelchair). Shoulder bracket 36 may also include any desired number of interior links 42, shown in FIG. 7. The links are pivotably connected to each other via any known hinge mechanism, which allows for shifting of the user's torso with respect to orthosis device 10 and misalignment between the user and orthosis device 10. As best shown in FIG. 4, links 38, 40, and 42 are hinged about a vertical axis, allowing for rotation of orthosis device about a vertical axis at a position generally corresponding to the anatomical shoulder.

Figure 8:
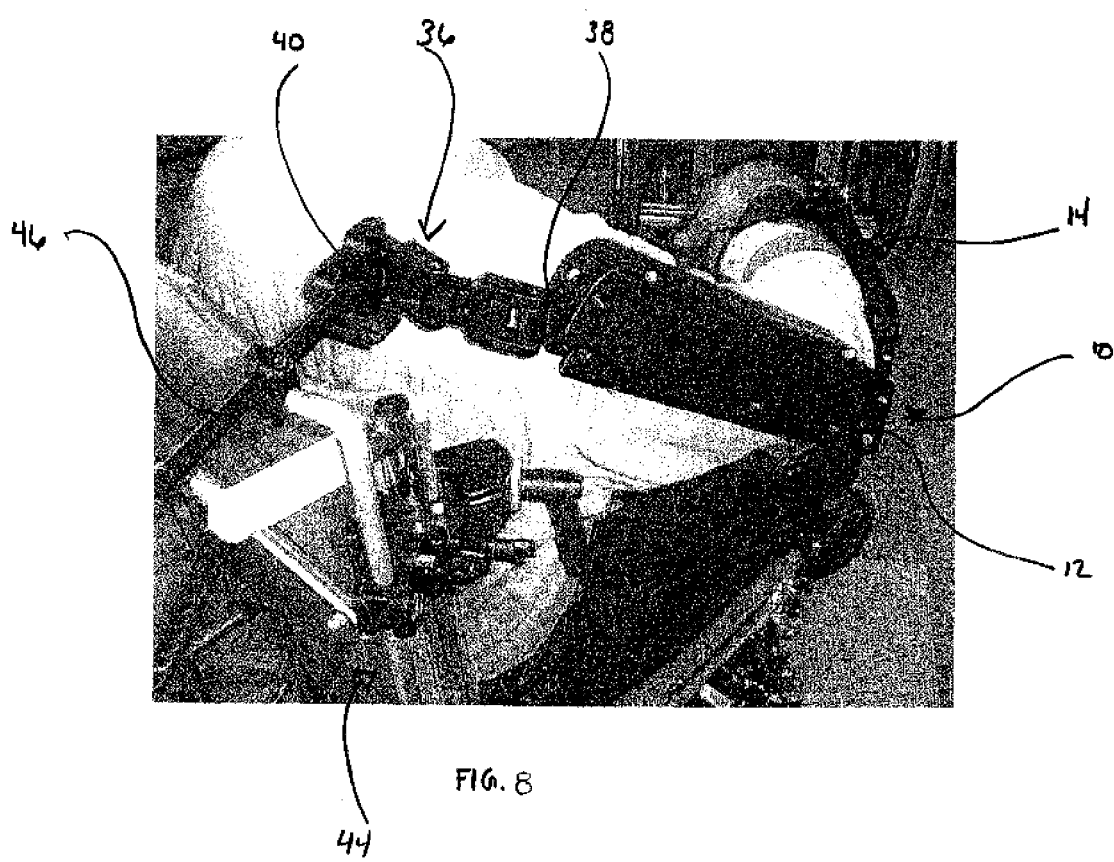
FIG. 8 illustrates the assistive medical system of the present invention.

Furthermore, by introducing additional degrees of freedom into the system, more natural movement of the limb within orthosis device 10 is facilitated. One skilled in the art will recognize that at least two pivotably connected links will be required, and that four pivotably connected links will provide enough additional degrees of freedom to achieve the desired level of mobility at the anatomical shoulder. Thus, as will be readily apparent to one skilled in the art, the orthosis device according to the present invention assists and augments anatomical motion in generally four degrees of freedom: rotation about horizontal and vertical axes at both the elbow and the shoulder. Free end 40 of shoulder bracket 36 may be directly attached to a wheelchair 44, or may be attached to a mounting bracket 46 in turn connected to wheelchair 44, as shown in FIG. 8.

Figure 9:
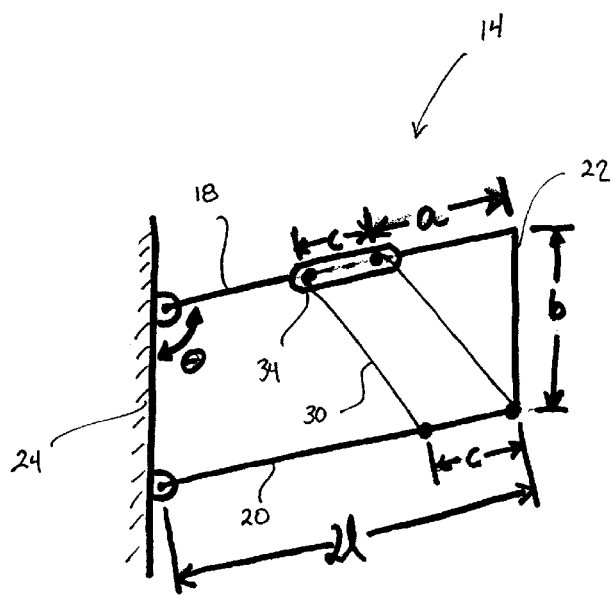
FIG. 9 is a schematic diagram of a limb section illustrating the selection of the dimensions for constructing and adjusting the orthosis device.
Figure 10:
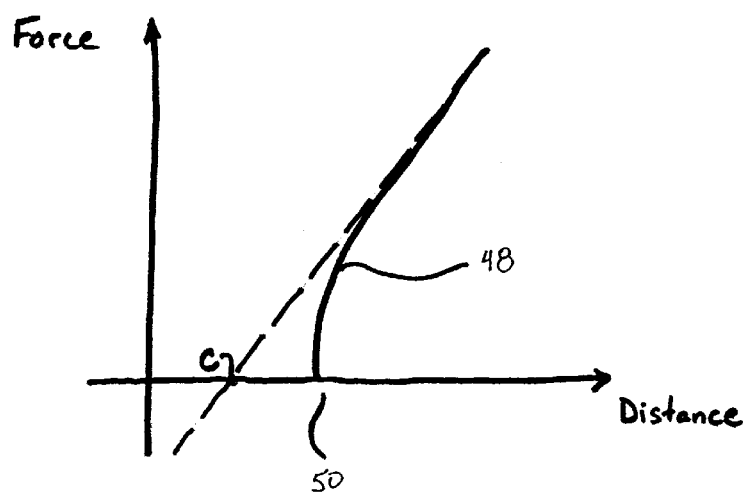
FIG. 10 is a graph illustrating the selection of the spring stiffness k of the spring member.

FIGS. 9 and 10 illustrate the selection of the dimensions and parameters used to construct and adjust orthosis device 10 for a particular individual. One skilled in the art will recognize that FIG. 9 is a schematic illustration of second limb section 14 according to the present invention, and that a similar schematic could be drawn for first limb section 12. Dimension 21 is the length of first and second links 18 and 20, dimension b is the length of third and fourth links 22 and 24, dimension c is the fixed distance between mounting posts 32, and dimension a is determined by the position of carriage 34 along first link 18. Angle θ varies as orthosis device 10 rotates about a horizontal axis in one degree of freedom. It should be noted that carriage 34 is fixed with respect to first link 18 as the angle θ changes; that is, dimension a is fixed as θ varies. Dimension a can, however, be varied to accommodate varying user weights (e.g., via the lead screw mechanism described above).

The choice of spring member 30 and dimensions a, b, and c are governed by the equation $$k = mgl/2ab, \quad (3)$$

where k is the stiffness of spring member 30, m is the combined mass of second limb section 14 and the limb inserted therein, and g is the gravitational constant. One skilled in the art will recognize that Equation 3 is derived from Equations 1 and 2, above, and that a similar equation can be derived for first limb section 12. Dimension c is chosen from a graph of the stiffness k of spring member 30, such as that shown in FIG. 10, where reference numeral 48 indicates the actual force-displacement curve for spring member 30, and reference numeral 50 denotes the unstretched length of spring member 30.

Once the appropriate dimensions and spring stiffness k have been selected and set, orthosis device 10 is configured to provide a gravity-balanced equilibrium to the user. That is, spring members 30 will offset the combined weight of orthosis device 10 and the limb of the user, thereby generally balancing the limb for all positions in three-dimensional space. This is analogous to movement in a zero-gravity environment, and will allow individuals with muscular degeneration to move their limbs to perform routine tasks (e.g., eating, shaving) with minimal effort.

As muscular disabilities are often progressive, however, the gravity-balancing provided by spring member 30 alone may not be sufficient to allow movement of the user's limb. Thus, orthosis device 10 may optionally be provided with powered actuators and force sensors (not shown). Force sensors detect the intention of the user to move in a particular direction in a fashion analogous to power steering in a vehicle. The force sensors then send a signal to activate the powered actuators. In this manner, the user is in control of the movement, but the necessary power to complete the movement is supplied by the powered actuators. Since orthosis device 10 inherently compensates for gravity, the powered actuators will require less power than existing powered orthoses, and may be powered, for example, by electric wheelchair batteries already present.

While the invention has been described in terms of its preferred embodiment, those skilled in the art will recognize that the invention can be practiced with modifications within the spirit and scope of the appended claims. Thus, it is intended that all matter contained in the foregoing description or shown in the accompanying drawings shall be interpreted as illustrative rather than limiting, and the invention should be defined only in accordance with the following claims and their equivalents.

What is claimed is:

1. An orthosis device for providing a gravity-balanced equilibrium for a limb of a user, said orthosis device comprising:

a first limb section and a second limb section, said first and second limb sections being pivotably connected in at least one degree of freedom;

said first and second limb sections each further comprising:

a first link and a second link, said first and second links being substantially parallel to each other;

a third link and a fourth link, said third and fourth links being substantially parallel to each other and pivotably connecting corresponding opposing ends of said first and second links to thereby define a four-bar linkage;

a first mounting mechanism attached to said first link and a second mounting mechanism attached to said second link, said first and second mounting mechanisms being offset from each other along a length of respective said first and second limb sections; and a spring member attaching between said first and second mounting mechanisms and being adapted to provide an equilibrium-inducing force corresponding to a combined weight of said limb section and the limb of the user.

2. The orthosis device according to claim 1, wherein said first mounting mechanism is provided on a carriage attached to said first link, a position of said carriage on said first link being adjustable along a length of said first link.

3. The orthosis device according to claim 2, wherein the position of said carriage on said first link is adjusted via a lead screw provided on said first link.

4. The orthosis device according to claim 2, wherein the position of said carriage on said first link is adjusted to pre-stress said spring member by an amount corresponding to the weight of the limb of the user.

5. The orthosis device according to claim 1, wherein said first and second mounting mechanisms each further comprise a pair of mounting posts, said mounting posts being disposed along a length of said first or second link and separated by a predetermined distance.

6. The orthosis device according to claim 5, wherein said distance is predetermined based on a spring stiffness of said spring member.

7. The orthosis device according to claim 5, wherein said spring member is comprised of an elastic cord stretched between said mounting posts of said first and second offset mounting mechanisms.

8. The orthosis device according to claim 1, wherein said first and second limb sections are pivotably connected in two degrees of freedom via an elbow joint.

9. The orthosis device according to claim 1, further comprising a shoulder bracket attached at an attached end to a proximal end of said first limb section and adapted at a free end for attachment to a chair.

10. The orthosis device according to claim 9, wherein said shoulder bracket is comprised of at least two links pivotably connected to each other.

11. The orthosis device according to claim 10, wherein said shoulder bracket is comprised of four links pivotably connected to each other.

12. The orthosis device according to claim 1, further comprising powered actuators and force sensors.

13. An assistive medical system, comprising:
    a wheelchair; and
    an orthosis device for providing a gravity-balanced equilibrium for the limb of the user, said orthosis device comprising:
        a first limb section and a second limb section pivotably connected to said first limb section;
        said first and second limb sections each further comprising:
            a first link and a second link, said first and second links being substantially parallel to each other;
            a third link and a fourth link, said third and fourth links being substantially parallel to each other and pivotably connecting corresponding opposing ends of said first and second links to thereby define a four-bar linkage;
            a first mounting mechanism and a second mounting mechanism attached to respective said first and second limb sections, a position of at least one of said first and second mounting mechanisms being adjustable to pre-stress said spring member;
            a spring member attached between said first and second mounting mechanisms and adapted to provide an equilibrium-inducing force corresponding to a combined weight of said limb section and the limb of the user; and
        a shoulder bracket attached to a proximal end of said orthosis device at a first end and attached to said wheelchair at a second end.

14. The assistive medical system according to claim 13, wherein said shoulder bracket is comprised of at least two links pivotably connected to each other.

15. The assistive medical system according to claim 14, wherein said shoulder bracket is comprised of four links pivotably connected to each other.

16. The assistive medical system according to claim 13, further comprising a mounting bracket attached to said wheelchair.

17. The assistive medical system according to claim 16, wherein said shoulder bracket attaches to said wheelchair via said mounting bracket.

18. The assistive medical system according to claim 13, wherein said first and second mounting mechanisms are attached to said first and second links, respectively, and are offset from each other along a length of said limb section.

19. The assistive medical system according to claim 13, wherein said orthosis device further comprises powered actuators and force sensors.

20. An orthosis device for use in an assistive medical system, said orthosis device comprising:
    a first limb section and a second limb section, said first and second limb sections being pivotably connected in two degrees of freedom via an elbow joint;
    said first and second limb sections each further comprising:
        a first link and a second link, said first and second links being substantially parallel to each other;
        a third link and a fourth link, said third and fourth links being substantially parallel to each other and pivotably connecting corresponding opposing ends of said first and second links to thereby define a four-bar linkage;
        a first mounting mechanism attached to said first link and a second mounting mechanism attached to said second link, said first and second mounting mechanisms being offset from each other along a length of respective said first and second limb sections;
        a spring member attached between said first and second mounting mechanisms and adapted to provide an equilibrium-inducing force corresponding to a combined weight of said limb section and a limb of a user; and
    a shoulder bracket attached at an attached end to a proximal end of said first limb section and adapted at a free end for attachment to a chair.

* * * * *